United States Patent [19]

Aslam et al.

[11] Patent Number: 5,041,571

[45] Date of Patent: Aug. 20, 1991

[54] PROCESS OF PRODUCING ANTHRAQUINONES IN ONE STEP

[75] Inventors: Mohammad Aslam, Corpus Christi, Tex.; Hans-Joachim Metz, Bensheim, Fed. Rep. of Germany

[73] Assignee: Hoechst Celanese Corporation, Somerville, N.J.

[21] Appl. No.: 503,490

[22] Filed: Mar. 29, 1990

[51] Int. Cl.[5] ............................................. C07C 50/18
[52] U.S. Cl. ..................................................... 552/268
[58] Field of Search ........................................ 552/268

[56] References Cited

U.S. PATENT DOCUMENTS

| | | | |
|---|---|---|---|
| 2,174,118 | 9/1939 | Calcott et al. | 552/268 |
| 4,379,092 | 4/1983 | Devic | 552/268 |
| 4,496,760 | 1/1985 | Devic | 552/268 |
| 4,591,460 | 5/1986 | Devic | 552/268 |

*Primary Examiner*—C. Warren Ivy
*Assistant Examiner*—Raymond Povington
*Attorney, Agent, or Firm*—Depaoli & O'Brien; Shirley L. Church

[57] ABSTRACT

A process for the preparation of anthraquinone compounds comprises reaction of phthalic anhydride with a benzene derivative in a reaction mixture containing HF and $BF_3$ as catalyst at a first temperature up to about 30° C. and, subsequently, at an elevated temperature.

8 Claims, No Drawings

PROCESS OF PRODUCING ANTHRAQUINONES IN ONE STEP

BACKGROUND OF THE INVENTION

The invention relates to a new process for the preparation of anthraquinones and substituted derivatives thereof having the general formula:

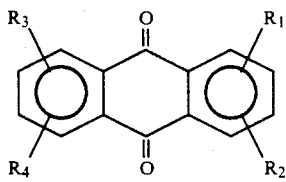
(I)

in which $R_1$, $R_2$, $R_3$ and $R_4$ each represent a hydrogen or halogen atom or a linear or branched alkyl group containing 1 to 5 carbon atoms. These compounds are used for dyestuffs, paper pulp industries and for the manufacture of hydrogen peroxide.

It is known that anthraquinone can be produced industrially by oxidation of anthracene. This process, however, is dependent upon problems of supply of anthracene from coal tar. It has been proposed to prepare anthraquinone from 1,4-naphthoquinone and butadiene (British Pat. No. 895,620) but the processes for obtaining 1,4-naphthoquinone are complicated and costly (British Patent No. 1,499,068).

Another much used industrial method enables anthraquinone and the substituted anthraquinones to be prepared from phthalic anhydride and benzene in the presence of aluminum chloride (U.S. Pat. No. 1,656,575), but this method has the disadvantage of the very considerable cost of the aluminum chloride which is consumed at the rate of 2 moles of aluminum chloride per mole of phthalic anhydride. In order to alleviate this disadvantage it has been proposed to react the gaseous mixture at high temperature over a solid catalyst based on a silico-aluminate (Japan Kokai Sho 49/30350 and Sho 59/95952) or on titanium oxide (Japan Kokai Sho 54/70252) but these processes impose the operation in the gaseous phase at high temperature and necessitate a complex installation with a costly investment.

More recently, U.S. Pat. No. 4,379,092 discloses forming anthraquinones by a two-step process. First, an equimolecular mixture of HF and $BF_3$ is used to catalyze the condensation of phthalic anhydride and benzene to o-benzoylbenzoic acid. The patent states that the reaction proceeds "rather surprisingly, without causing cyclization of the benzoylbenzoic acid which is formed, therefore without liberating a molecule of water which would hydrolyze or hydrate $BF_3$ and thus make the recovery of the catalyst difficult." Moreover, the patent states the fact that the equimolecular mixture of HF and $BF_3$ does not cause cyclization is quite unexpected since the cyclization of benzoylbenzoic acid to anthraquinone takes place in anhydrous HF (U.S. Pat. No. 2,174,118). Secondly, the pure o-benzoylbenzoic acid is obtained by extraction of the crude reaction mixture with boiling water, followed by recrystallization by cooling and conversion of the o-benzoylbenzoic acid into the anthraquinone by heating in concentrated sulfuric acid or by any other means of cyclization known in the art. The cyclization may take place in the course of the production of intermediate anthraquinone compounds for dyes wherein the sulfonation and nitration reactions take place in a cyclizing medium, for example $H_2SO_4$ or HF.

While the process described in U.S. Pat. No. 4,379,092 for producing anthraquinone compounds is useful, the need to separate the benzoylbenzoic acid from the reaction medium for subsequent cyclization is a disadvantage and adds additional costs to the overall process. Accordingly, it is an object of the present invention to produce anthraquinones by the condensation of phthalic anhydride and benzene compounds and avoid the separation and recovery of intermediate products.

SUMMARY OF THE INVENTION

In accordance with the present invention, anthraquinones are formed by the condensation of phthalic anhydride and a benzene compound in the presence of HF and $BF_3$ in a process comprising subjecting the reaction mixture to a first low temperature stage and, subsequently, subjecting the reaction mixture to an elevated temperature stage to produce anthraquinone. In the process of the present invention, the molar ratio of HF to $BF_3$ is preferably at least 2.

DETAILED DESCRIPTION OF THE INVENTION

The present invention therefore relates to a process for the preparation of compounds of general formula (I) which comprises reacting phthalic anhydride which can be substituted of the formula:

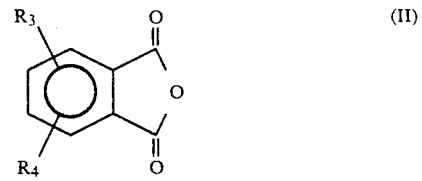
(II)

with a benzene compound of the general formula:

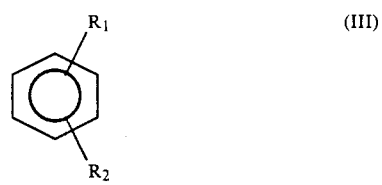
(III)

in which $R_1$, $R_2$ and $R_3$ and $R_4$ have the same definitions as the above in the presence of a catalyst comprising a mixture of hydrofluoric acid and boron trifluoride and in which two separate temperature regimes are used to form an anthraquinone of formula I.

With respect to the catalyst, the amount of $BF_3$ present in the reaction mixture must be greater than 3 moles per mole of phthalic anhydride; the preferred ratio is between 5 and 20 moles of $BF_3$ per mole of phthalic anhydride. The molar ratio of HF to $BF_3$ may be near to 1, but, the preferred ratio is between 2 and 12. A most preferred molar ratio of HF to $BF_3$ is about 4 to 10.

Since the catalyst also takes the place of a solvent for the reaction, it must be used in sufficient quantity to make the reaction mass fluid, for example, from 10 to 50 moles of HF per mole of phthalic anhydride. This amount may be reduced by the use of a third solvent which is inert under the conditions of the reaction. As inert solvents methylene chloride and other halogenated hydrocarbons may be used.

The phthalic anhydride and the aromatic derivative of formula (III) are employed at the rate of 0.9 to 1.2 moles of compound (III) per mole of phthalic anhydride. In order to reduce the formation of by-products, it is preferred to use 1 to 1.1 mole of benzene compound per mole of phthalic anhydride. Excess of benzenic compound favors the formation of the phenyl-phthalide derivatives.

The reaction is effected at two separate temperatures. In the initial stage, a temperature from about $-60°$ C. to $+30°$ C. is used. During this first stage, temperatures over 30° C. may increase the quantity of by-products of the phenyl-phthalide type and should be avoided. The length of the first stage of the reaction is between 5 and 60 minutes according to the temperature. The reaction takes place under a pressure of 5 to 60 bars according to the temperature.

The second stage of the reaction involves elevating the temperature of the reaction mixture. No separation of products need take place between the reaction stages. Thus, in the second stage of the reaction, the temperature of the reaction mixture is raised to about 40°–70° C. and maintained at such temperature for about 1 to 6 hours to afford anthraquinones.

At the end of the reaction, the greater part of the catalyst is recovered by distillation under reduced pressure or the catalyst can be simply vented from the reaction apparatus by means of an inert gas purge. The anthraquinone product is then neutralized with an aqueous solution of a base such as sodium hydroxide. The product from the reaction forms a phase immiscible with water and can be collected by decantation or by filtration.

The following examples illustrate the present invention without it being limited thereto. In the examples and throughout the specification and claims, all parts and percentages are by weight unless otherwise specified.

EXAMPLE 1

Phthalic anhydride (14.8 g, 0.1 mol), HF (80 g, 4.0 mol) and BF3 (34 g, 0.5 mol) were mixed in a Hastelloy-c autoclave (300 cc). The reactor was cooled to 0° C. and benzene (7.8 g, 0.10 mol) was pumped in slowly. The mixture was stirred at 0° C. for 1 hr. and then at 50° C. for 4 hr. The reaction mixture was neutralized with NaOH to give a black precipitate. The precipitate was dried in a vacuum oven to afford a gray solid (20.0 g). Lc-analysis of the solid indicated the presence of mainly anthraquinone. The reaction went with complete conversion and 64% selectivity to anthraquinone. Anthraquinones yield (61%).

EXAMPLE 2

Phthalic anhydride (14.8 g, 0.1 mol), HF (90 g, 4.5 mol) and BF3 (34 g, 0.5 mol) were mixed in a Hastelloy-c autoclave (300 cc). The reactor was cooled to 0° C. and toluene (10.1 g, 0.11 mol) was pumped in slowly. The mixture was stirred at 0° C. for 1 h and 60° C. for 3 h. The reaction mixture was neutralized with NaOH to give a black precipitate. The precipitate was dried in a vacuum oven to afford a gray solid (20.9 g). LC-analysis of the solid indicated the presence of mainly 2-methyl anthraquinone and small amount of 1-methyl anthraquinone. The reaction went with 95% conversion and 58% selectively to 2-methyl anthraquinone, 8% selectivity to 1-methyl anthraquinone.

What is claimed is:

1. In the process for the preparation of anthraquinone compounds of the general formula:

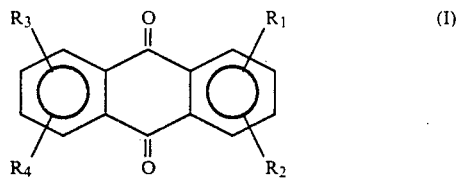

in which $R_1$, $R_2$, $R_3$ and $R_4$ represent hydrogen or a linear or branched alkyl group containing 1 to 5 carbon atoms, which process comprises a first reaction of a phthalic anhydride or substituted phthalic anhydride of the formula:

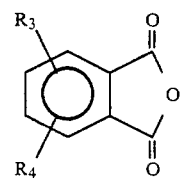

with a benzene compound of the general formula:

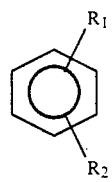

in which $R_1$, $R_2$, $R_3$ and $R_4$ have the same definition as above, in a first reaction mixture containing a catalyst mixture of HF and $BF_3$, separating an intermediate product capable of being cyclized to anthraquinones and cyclizing the separated product in a second reaction to yield a compound of formula (I), the improvement which comprises subjecting said first reaction mixture to a first temperature of from about $-60°$ to about 30° C. for up to about 1 hour and then subjecting said first reaction mixture to an elevated temperature above said first temperature without separation of said intermediate product capable of being cyclized to anthraquinones whereby a product containing said anthraquinone compounds as the major component thereof is formed.

2. The process according to claim 1 wherein the $HF/BF_3$ molar ratio is about 2 to 12.

3. The process according to claim 2 wherein the $HF/BF_3$ molar ratio is about 4 to 10.

4. The process according to claim 1 wherein from 0.9 to 1.2 moles of said benzene compound are used per mole of said phthalic anhydride.

5. The process according to claims 1, 2 or 3 wherein the reaction between said phthalic anhydride and said benzene compound is carried out at said first temperature for about 5 to 60 minutes.

6. The process according to claim 5 wherein said first temperature is 0° C.

7. The process of claims 1, 2 or 3 wherein said elevated temperature is from about 40° to 70° C. and maintaining said elevated temperature for 1 to 6 hours.

8. The process according to claim 1 wherein at least 3 moles of $BF_3$ are utilized per mole of phthalic anhydride.

* * * * *